United States Patent
Andersen et al.

(10) Patent No.: US 12,426,986 B2
(45) Date of Patent: Sep. 30, 2025

(54) BALANCING, POSITIONING AND FIXATING ASSEMBLY

(71) Applicants: MAGVENTURE A/S, Farum (DK); TONICA ELEKTRONIK A/S, Farum (DK)

(72) Inventors: Stig Wanding Andersen, Farum (DK); Claus Mathiesen, Farum (DK); Lone Nitsche Damgård Jacobsen, Farum (DK)

(73) Assignees: MAGVENTURE A/S, Farum (DK); TONICA ELEKTRONIK A/S, Farum (DK)

(*) Notice: Subject to any disclaimer, the term of this patent is extended or adjusted under 35 U.S.C. 154(b) by 123 days.

(21) Appl. No.: 18/257,835

(22) PCT Filed: Dec. 14, 2021

(86) PCT No.: PCT/EP2021/085608
§ 371 (c)(1),
(2) Date: Jun. 15, 2023

(87) PCT Pub. No.: WO2022/128991
PCT Pub. Date: Jun. 23, 2022

(65) Prior Publication Data
US 2024/0090970 A1    Mar. 21, 2024

Related U.S. Application Data

(60) Provisional application No. 63/125,594, filed on Dec. 15, 2020.

(30) Foreign Application Priority Data

Dec. 15, 2020   (EP) .................................... 20214073

(51) Int. Cl.
A61B 90/50     (2016.01)
A61B 50/10     (2016.01)
A61N 2/02      (2006.01)

(52) U.S. Cl.
CPC .............. *A61B 90/50* (2016.02); *A61B 50/10* (2016.02); *A61N 2/02* (2013.01)

(58) Field of Classification Search
CPC ........... F16M 11/2092; F16M 11/2014; F16M 11/14; F16M 11/28; F16M 11/24;
(Continued)

(56) References Cited

U.S. PATENT DOCUMENTS 6,012,693 A * 1/2000 Voeller ................. F16M 11/048
248/920
6,763,286 B2 * 7/2004 Metelski ............ F16M 11/2064
248/162.1
(Continued)

FOREIGN PATENT DOCUMENTS

EP      1283970 A1    2/2003
FR      2722893 A1    1/1996
(Continued)

OTHER PUBLICATIONS

International Preliminary Report on Patentability mailed Jun. 13, 2023 in International Application No. PCT/EP2021/085608, 7 pages.
(Continued)

*Primary Examiner* — Eret C McNichols
(74) *Attorney, Agent, or Firm* — Nixon & Vanderhye P.C.

(57) ABSTRACT

The present invention relates to a balancing, positioning and fixating assembly for balancing a treatment device, comprising balance arm having a first arm end and a second arm end, a stepper part having a first part end and a second part end, the first arm end is connected with the second part end via a first pivot joint so that the balance arm is movable in
(Continued)

Figure 1:
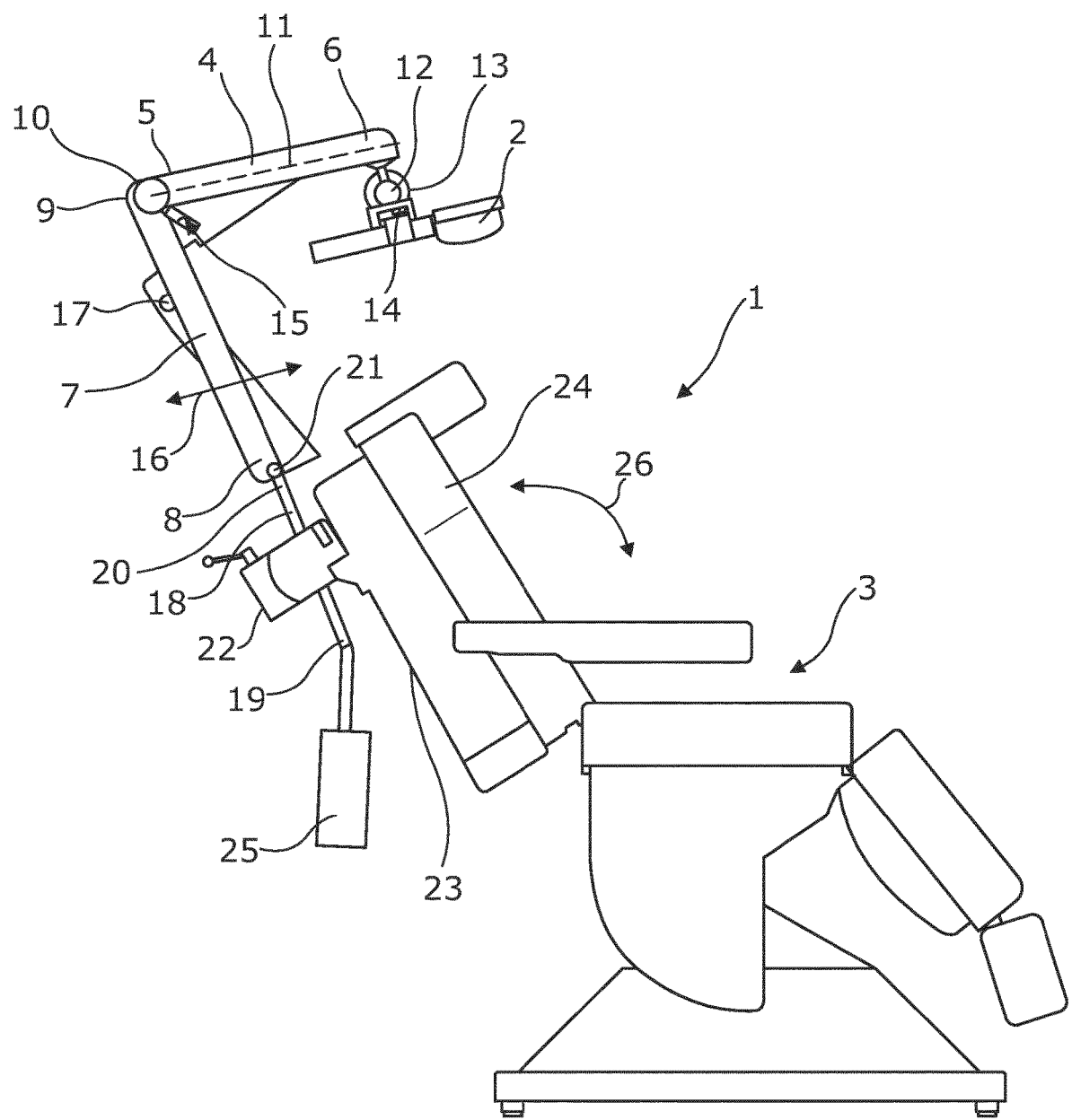

relation to the stepper part, and an angulator device is arranged in connection with the second arm end, the angulator device is configured to connect the treatment device to the balance arm and to facilitate movement of the treatment device in different angles, wherein a spring device having a predetermined spring force is arranged along the balance arm, the spring device has a first spring end and a second spring end.

21 Claims, 5 Drawing Sheets

(58) Field of Classification Search
CPC ....... F16M 2200/044; F16M 2200/048; F16M 2200/063; F16M 13/022; A61B 90/50; A61B 50/10; A61N 2/02
See application file for complete search history.

(56) References Cited

U.S. PATENT DOCUMENTS

| | | | | |
|---|---|---|---|---|
| 7,100,880 | B2 * | 9/2006 | Oddsen, Jr. | F16M 11/10 248/278.1 |
| 7,207,531 | B2 | 4/2007 | Piontkowski | |
| 7,255,311 | B2 * | 8/2007 | Metelski | F16M 11/2064 248/123.11 |
| 7,325,777 | B2 * | 2/2008 | Thiessen | B25H 1/0021 248/278.1 |
| 8,342,467 | B2 * | 1/2013 | Stachowski | F16M 13/02 248/281.11 |
| 10,760,731 | B2 * | 9/2020 | Chang | F16F 9/0245 |
| 10,914,420 | B2 * | 2/2021 | Hung | F16M 11/2092 |
| 10,976,001 | B2 * | 4/2021 | Hung | F16M 11/2014 |
| 11,035,518 | B2 * | 6/2021 | Hung | F16M 11/048 |
| 11,131,421 | B2 * | 9/2021 | Hung | F16M 11/2021 |
| 11,131,423 | B2 * | 9/2021 | Anderson | F16M 11/10 |
| 11,629,770 | B2 * | 4/2023 | Huang | F16C 32/0603 267/118 |
| 12,152,720 | B1 * | 11/2024 | Massey | F16M 11/041 |
| 2005/0224664 | A1 * | 10/2005 | Metelski | F16M 11/18 248/123.11 |
| 2005/0284991 | A1 | 12/2005 | Saez | |
| 2008/0054133 | A1 * | 3/2008 | Huang | F16M 11/2064 248/178.1 |
| 2016/0116108 | A1 * | 4/2016 | Borloz | F16M 13/02 248/284.1 |
| 2020/0049307 | A1 * | 2/2020 | Hung | F16M 11/24 |
| 2022/0356986 | A1 * | 11/2022 | You | F16M 11/24 |

FOREIGN PATENT DOCUMENTS

| | | |
|---|---|---|
| JP | H04505798 A | 10/1992 |
| WO | 9100472 A1 | 1/1991 |
| WO | 0190630 A1 | 11/2001 |

OTHER PUBLICATIONS

International Search Report and Written Opinion of the ISA for PCT/EP2021/085608 mailed May 31, 2022, 13 pages.

* cited by examiner

BALANCING, POSITIONING AND FIXATING ASSEMBLY

This application is the U.S. national phase of International Application No. PCT/EP2021/085608 filed Dec. 14, 2021 which designated the U.S. and claims priority to EP 20214073.7 filed Dec. 15, 2020 and U.S. 63/125,594 filed Dec. 15, 2020, the entire contents of each of which are hereby incorporated by reference.

The present invention relates to a balancing, positioning and fixating assembly for balancing a treatment device.

Assemblies for balancing, positioning and fixating different treatment devices are known. However, the known assemblies require many adjustments when one treatment device is replaced with another. Hence, the operator of the assembly and the treatment device often uses a lot of strength in holding and adjusting the assembly as well as when the treatment device is being used. Also, the known assemblies often do not provide good ergonomic positions for the operator of the treatment device.

It is an object of the present invention to wholly or partly overcome the above disadvantages and drawbacks of the prior art. More specifically, it is an object to provide an improved balancing, positioning and fixating assembly with a high usability and flexibility, and still providing enhanced ergonomic positions for the operator during use.

The above objects, together with numerous other objects, advantages and features, which will become evident from the below description, are accomplished by a solution in accordance with the present invention by a balancing, positioning and fixating assembly for balancing a treatment device, comprising a balance arm having a first arm end and a second arm end, a stepper part having a first part end and a second part end, the first arm end is connected with the second part end via a first pivot joint so that the balance arm is movable in relation to the stepper part, and an angulator device is arranged in connection with the second arm end, the angulator device is configured to connect the treatment device to the balance arm and to facilitate movement of the treatment device in different angles, wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm.

Hereby is obtained, that different treatment devices having different weights may be mounted and used with the balancing, positioning and fixating assembly and still being hold and maintained in the right position. Thus, by arranging the spring device in different angles it is possible in an expedient manner to balance different weights of the treatment device. Hereby a higher degree of flexibility is obtained compared to prior solutions while still ensuring good ergonomic working positions for the operator during use.

Furthermore, the spring device may be a gas spring.

In addition, the predetermined spring force may be at least 150 N.

Also, the variable connection may be stepless or may have a plurality of predetermined positions.

Moreover, each predetermined position of the variable connection may correspond to a weight of the treatment device so that the treatment device is balanced to a degree wherein it exerts a slight pressure to a head of a patient.

Furthermore, the angles may be between 3 degrees and 20 degrees.

In addition, the variable connection may comprise a connection member being arranged at the first arm end, the connection member is configured to receive the first spring end.

The connection member may comprise a recess wherein a pin of the first spring end is movable arranged.

Also, the recess may have an extension extending away from the balance arm in an angle compared to the longitudinal axis of the balance arm.

Moreover, the recess may have a plurality of indentations arranged along the extension of the recess, the pin is configured to be moved into one of the indentations and thereby position the spring device in the intended angle in relation to the longitudinal axis.

The connection member may be connected to the second part end and is connected to the first arm end via the first pivot joint. Hence, the connection member may be configured to connect the second part end and the first arm end.

Furthermore, the spring device may comprise a spring coil, a hydraulic cylinder, or similar spring-loaded elements.

Additionally, the connection member may be operatively connected with a control unit.

The control unit may be configured to position the spring device in an angle by instruction of an operator, or automatically by identifying a weight of the treatment device.

Moreover, the angulator device may comprise a ball joint enabling the treatment device to be moved around the ball joint in any angle.

Also, the angulator device may comprise a mounting part being configured to receive a corresponding mounting member arranged on the treatment device so that the treatment device is releasable mounted to the angulator device.

Furthermore, the mounting part may comprise a locking mechanism for locking the treatment device to the angulator device.

In addition, the stepper part may be configured to be moved in a direction being parallel to the longitudinal axis and between a first extreme position and a second extreme position.

Moreover, the stepper part may comprise a locking pin being configured to lock the stepper part in either the first extreme position or the second extreme position or any positions therebetween.

The balancing, positioning and fixating assembly may further comprise a slide part having a first slide end and a second slide end, the first part end of the stepper part is connected with the second slide end via a second pivot joint.

Also, a movement member may be arranged between the first slide end and the second slide end, the movement member is configured to releasable maintain the slide part in an intended position.

The movement member may have a first position wherein the slide part is securely fastened and a second position wherein the slide part is movable.

Furthermore, a locking member may be configured to lock the movable member in the first position.

Moreover, the movement member may be configured to allow intermediate positions.

Also, the locking member may comprise a handle to manually controlling the locking member.

Furthermore, the locking member may be operatively connected with control device, the control device being configured to allowing the slide part to be moved with activation, and to lock the slide part in position when the control device is deactivated.

Additionally, the movement member may comprise a ball wherethrough the slide part is extending.

Moreover, the ball may be movable within a housing.

Also, restrictions in movement of the slide part may be obtained by a predetermined opening in the housing, the slide part is extending through the opening and will be restricted in further movement by a circumference of the opening in all directions so that when the slide part abuts the circumference it is hindered in being moved further.

The slide part may be movable in all directions within the opening.

Furthermore, a counterweight may be connected with the first slide end.

Also, a weight of the counterweight may be larger than 5 kg, preferably larger than 8 kg.

In addition, the counterweight may be securely fastened to the slide part at least in a sideway direction.

Moreover, the first pivot joint and the second pivot joint may comprise a ball bearing or a roller bearing.

The balancing, positioning and fixating assembly may further comprise a chair.

Furthermore, the movement member may be configured to be securely mounted on a back of a backrest of the chair. An angle of the backrest may be adjustable.

Additionally, the treatment device may be a coil.

The coil is configured to Transcranial magnetic stimulation (TMS).

Also, the coil may have a coil weight of more than 1.5 kg

Moreover, the coil may be operatively connected with a magnetic stimulator.

Furthermore, the assembly may comprise a base or trolley for supporting the assembly, the base or trolley having wheels so that the assembly can be positioned in intended position.

Figure 2:
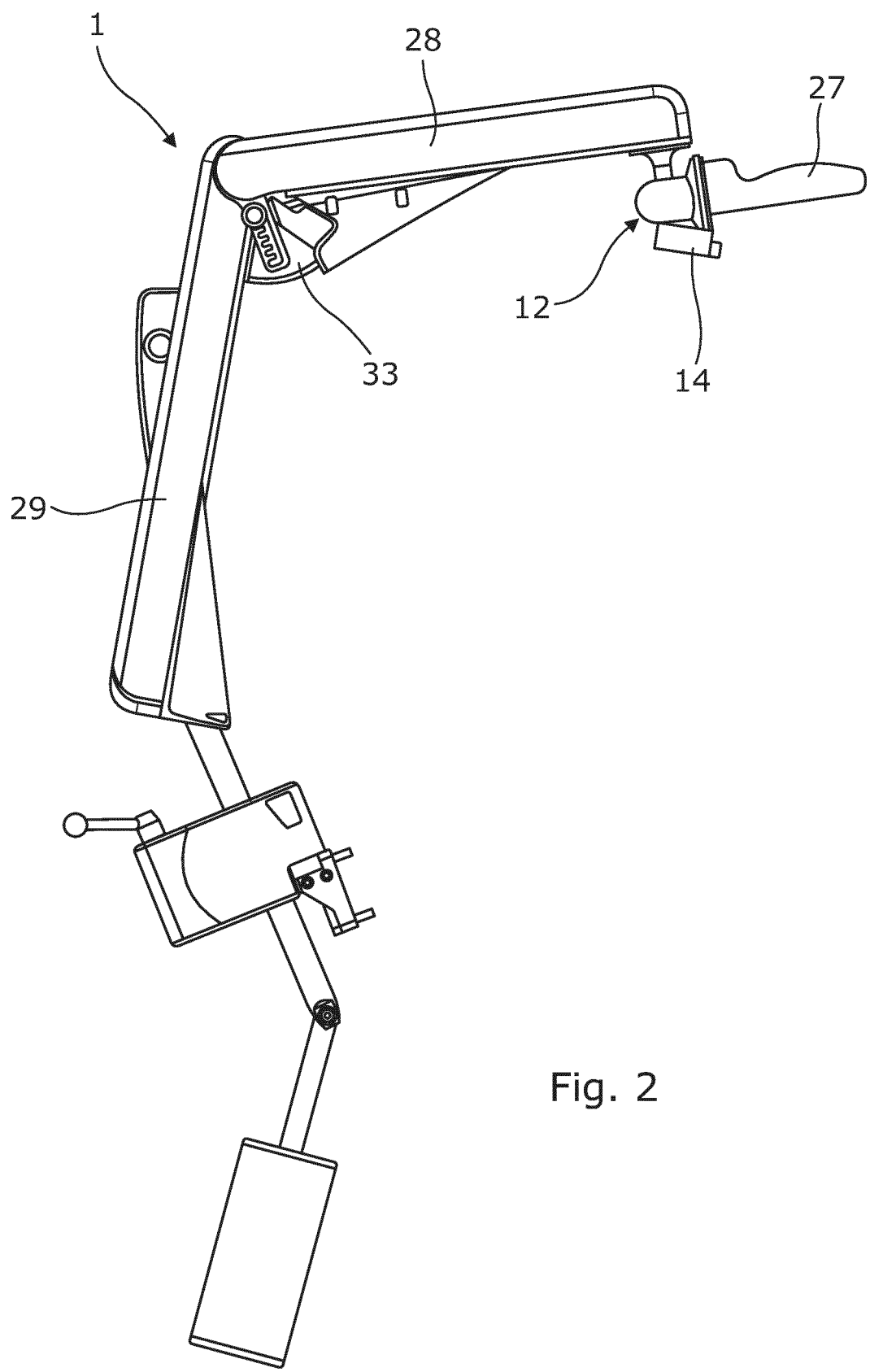
Figure 3:
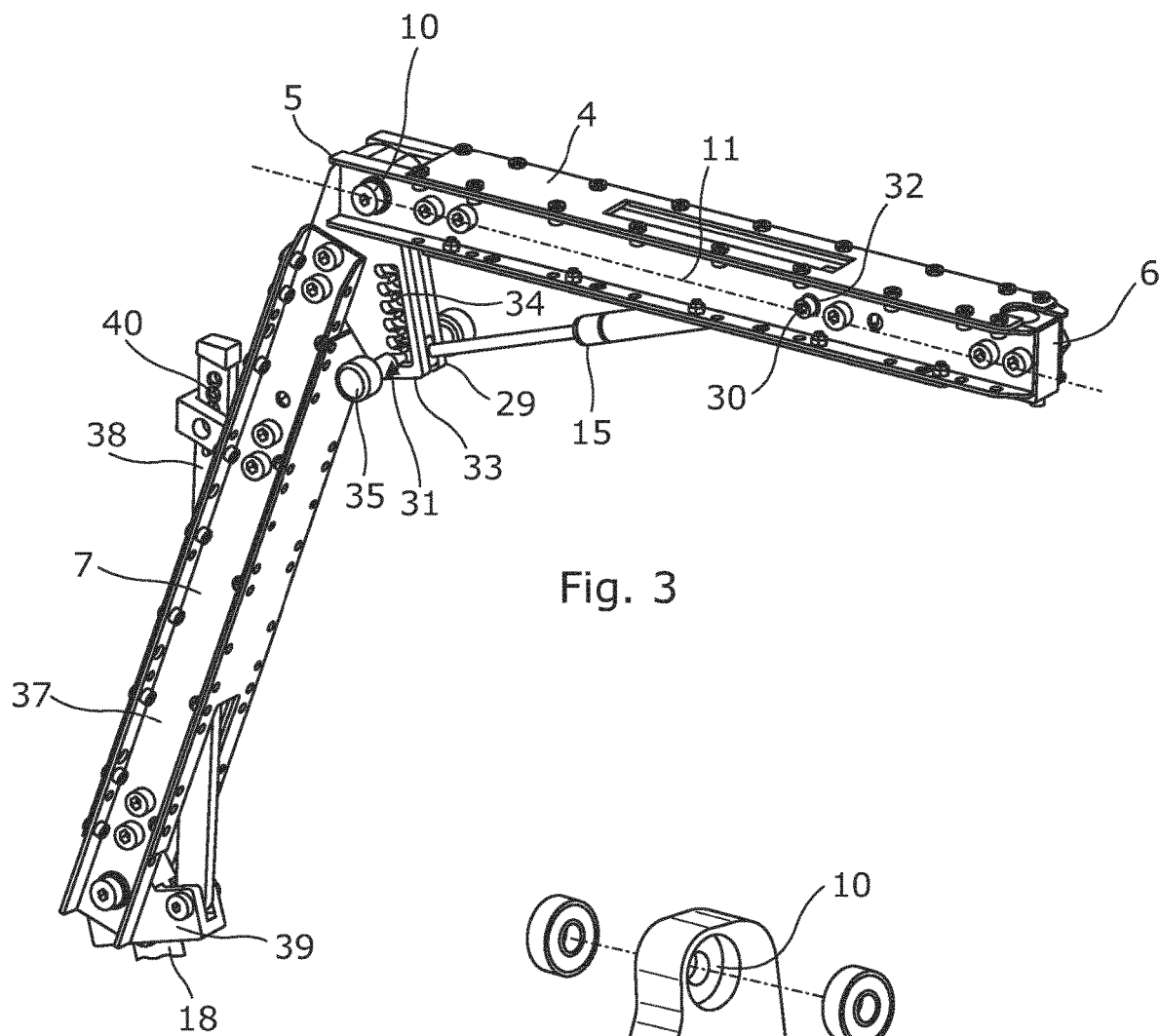
Figure 4:
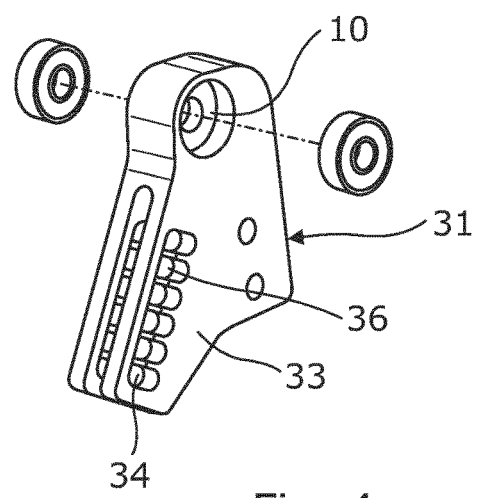
Figure 5:
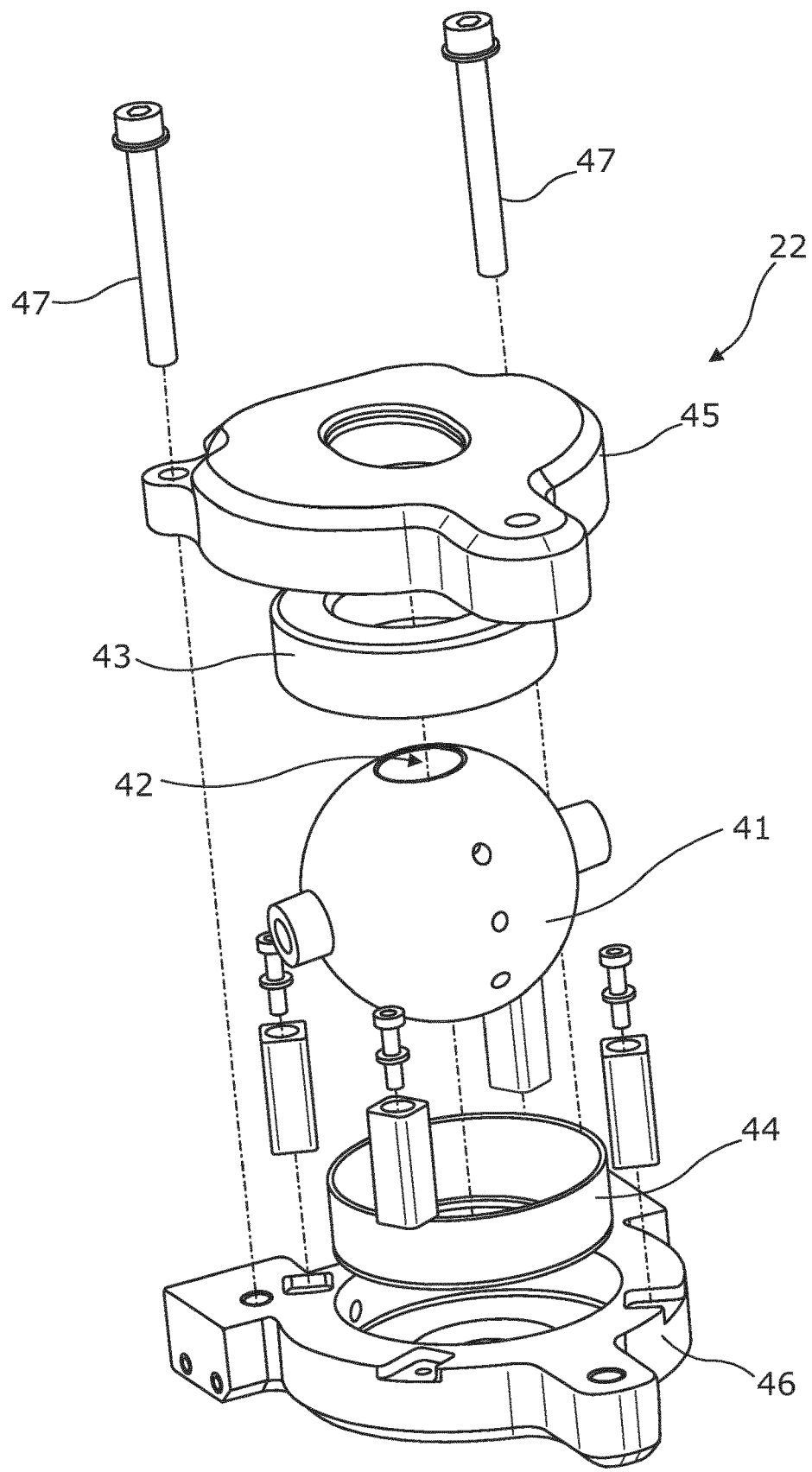
Figure 6:
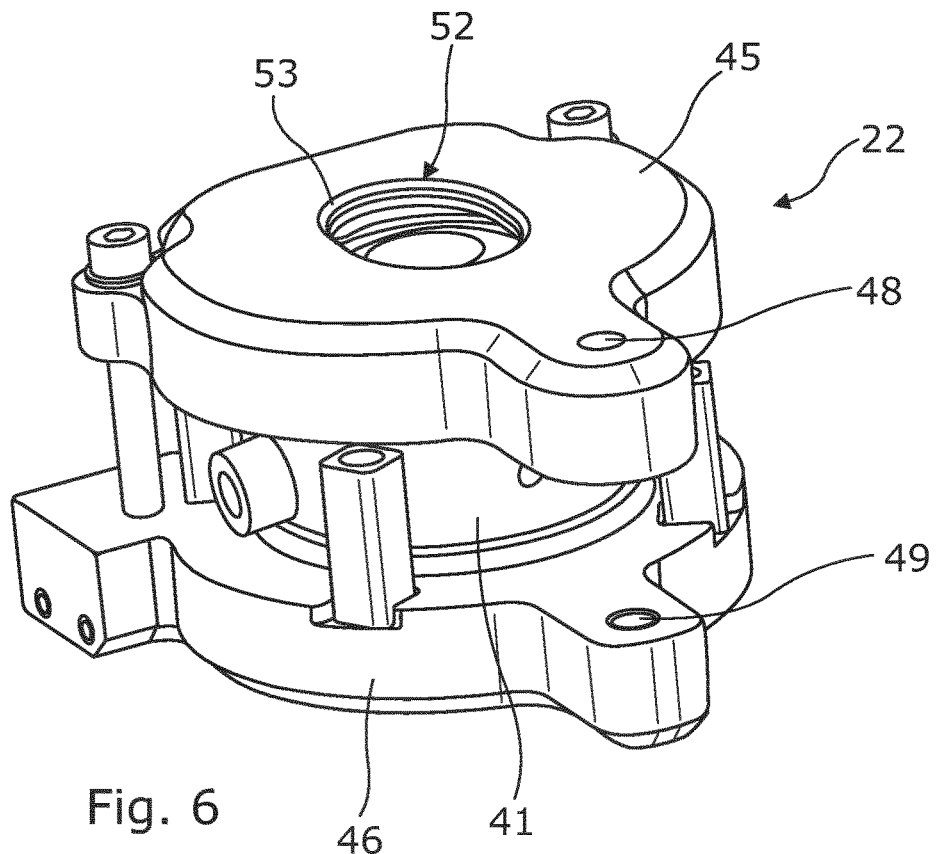
Figure 7:
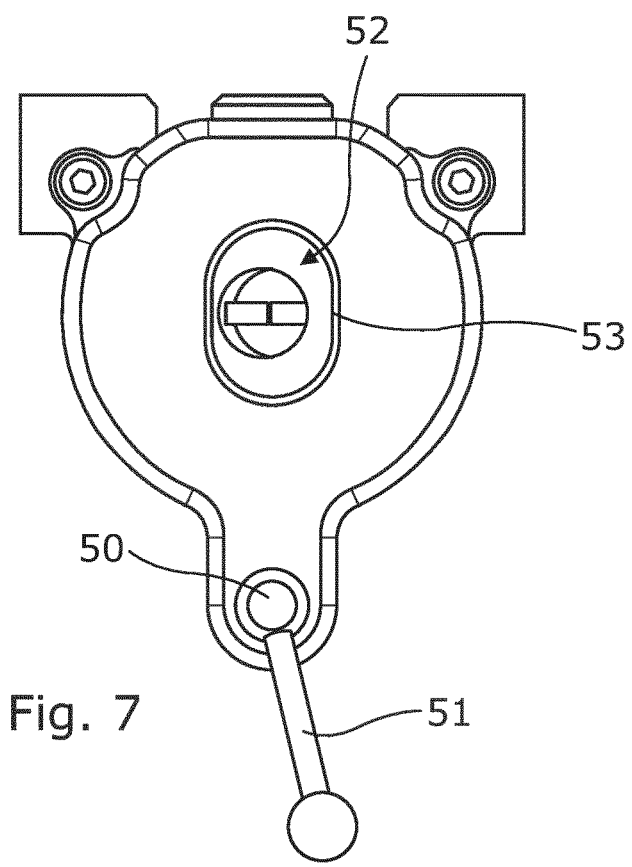

The invention and its many advantages will be described in more detail below with reference to the accompanying schematic drawings, which for the purpose of illustration show some non-limiting embodiments and in which FIG. 1 shows an embodiment of a balancing, positioning and fixating assembly according to the present invention, FIG. 2 shows a side view of a balancing, positioning and fixating assembly, FIG. 3 shows the balance arm and the stepper part, FIG. 4 shows a variable connection, and FIGS. 5-7 show an embodiment of the slide part and movement member.

All the figures are highly schematic and not necessarily to scale, and they show only those parts which are necessary in order to elucidate the invention, other parts being omitted or merely suggested.

FIG. 1 show a balancing, positioning and fixating assembly 1 for balancing a treatment device 2 according to the present invention. The balancing, positioning and fixating assembly comprises in the present embodiment a chair 3, and the present invention will mainly be described in connection with the chair 3. However, as will be appreciated by the skilled person, the balancing, positioning and fixating assembly 1 may also comprise a base or a trolley to support the assembly during storage and use.

The treatment device 2 may be a coil as shown in FIG. 1, however it may also be other treatment devices or tools being used to different applications and purposes wherein an operator is operating the treatment device 2.

According to the invention, the balancing positioning and fixating assembly 1 comprises a balance arm 4 having a first arm end 5 and a second arm end 6, and a stepper part 7 having a first part end 8 and a second part end 9. The first arm end 5 is connected with the second part end 9 via a first pivot joint 10 so that the balance arm 4 can be moved in relation to the stepper part 7 around the pivot joint 10. The balance arm 4 has a longitudinal axis 11 extending along the balance arm 4.

In addition, an angulator device 12 is arranged in connection with the second arm end 6, the angulator device 12 is configured to connect the treatment device 2 to the balance arm 4 and to facilitate movement of the treatment device 2 in different angles. The angulator device 12 is in present embodiment arranged beneath the balance arm 4 at the second arm end, however, in other embodiments it may be connected with the balance arm at other positions. The angulator device 12 comprises a ball joint 13 enabling the treatment device 2 to be moved around the ball joint 13 in any angle. The angulator device 12 may also comprise a mounting part 14 being configured to receive a corresponding mounting member arranged on the treatment device 2 so that the treatment device is 2 releasable mounted to the angulator device 12. Hereby is obtained that the treatment device 2 may be replaced easily. Also, the mounting part 24 may comprise a locking mechanism (not shown) for locking the treatment device 2 to the angulator device 12 whereby it is ensured that the treatment device 2 is securely maintained during handling and use of the treatment device 2.

Furthermore, a spring device 15 (as seen in FIG. 3) having a predetermined spring force is arranged along the balance arm 4. The spring device 15 will be further described in connection with FIG. 3 below. According to the inventive idea, the spring device 15 has a first spring end and a second spring end, the second spring end is fixedly connected to the balance arm 4 closer to the second arm end 6 than the first arm end 5, and the first spring end is connected with the first arm end via a variable connection so that the spring device 15 can be arranged in different angles compared to a longitudinal axis 11 of the balance arm 4. Hereby is obtained, that different treatment devices 2 having different weights may be mounted and used with the assembly 1 and still being hold and maintained in the right position. Thus, by arranging the spring device 15 in different angles it is possible in an expedient manner to balance different weights of the treatment device 2. Hereby a higher degree of flexibility is obtained compared to prior solutions.

The stepper part 7 is configured to be moved in a direction forth and back as indicated by arrow 16 and is configured to be moved between a first extreme position and a second extreme position. Furthermore, the stepper part 7 comprises a locking pin 17 being configured to lock the stepper part 7 either in the first extreme position or in the second extreme position or in any positions therebetween.

In addition, a slide part 18 having a first slide end 19 and a second slide end 20, the first part end 8 of the stepper part 7 is connected with the second slide end 20 via a second pivot joint 21. When stepper part 7 is being moved it is turning around the second pivot joint 21.

The slide part 18 is in present embodiment a rod and is securely fasten to a movement member 22. In other not shown embodiments the slide part 18 may be movable in the movement member 22.

The movement member 22 is in the present embodiment arranged on a back 23 of a backrest 24 of the chair 3 so that the stepper part and balance arm may be positioned in relation to a person sitting in the chair 3. Furthermore, the backrest 24 may be moved into different angle positions as indicated with arrow 26 whereby the balancing, positioning and fixating assembly 1 facilitates positioning and balancing of the treatment device 2 in view of inclination of the backrest, height of the person, and weight of the treatment device without jeopardizing ergonomic correct working positions for the operator both during initial adjustments of the assembly 1 and subsequently during using the treatment device 2.

The movement member 22 is arranged between the first slide end 19 and the second slide end 20, the movement member is configured to releasable maintain the slide part 18 in an intended position. In the present embodiment, the slide part 18 is configured to be movable in 360 degrees around a vertical plane while being maintained in the same vertical height where connected to the movement member 22. This will be further described below.

In the present embodiment wherein the backrest 24 may be angled it is obtained that the treatment device 2 may be balanced and positioned at the intended positions in relation to for instance a person to be treated. By the present assembly 1, the operator has a flexible assembly 1 with many adjustment possibilities in relation to treatment target and the height of the person to treated as well as the height of the operator. In addition, the operator will be able to have an ergonomic correct working position without stressing the body by varying the positions of the treatment device 2.

Furthermore, a counterweight 25 is connected with the first slide end 19. The weight of the counterweight 25 is larger than 5 kg, preferably larger than 8 kg.

The counterweight 25 is securely fastened to the slide part at least in a sideway direction but may also be movable forth and back in a direction being perpendicular to the sideway direction. The counterweight 25 is configured to balance the stepper part 7, the balance arm 4 and the treatment device 2 when they are being moved either to an initial position or during movement of the treatment device 2 in different angles and/or directions. The counterweight 25 ensures that a state of equilibrium is instantly obtained without any larger movement between mutual components of the assembly 1 and/or their inertia.

In FIG. 2, the balancing, positioning and fixating assembly 1 of FIG. 1 is shown in a side view without the chair. The angulator device 12 also comprise a device handle 27 enabling the operator to move the treatment device (not shown) to the intended position. One embodiment of the mounting part 14 is shown wherein the mounting member of the treatment device may be connected so that the angulator device 12 and the treatment device is mechanically locked to each other.

The different components of the balancing, positioning and fixating assembly 1 may be covered by separate covers 28, 29 so that the interior of the different components is protected and for providing an appearance to the balancing, positioning and fixating assembly 1.

In FIG. 3 the balance arm 4 and the stepper part 7 are shown with the covers removed. The spring device 15 has a first spring end 29 and a second spring end 30, the second spring end 30 is fixedly connected to the balance arm 4 closer to the second arm end 6 than the first arm end 5, and the first spring end 29 is connected with the first arm end 5 via a variable connection 31 so that the spring device 15 can be arranged in different angles compared to the longitudinal axis 11 of the balance arm 4. Even though the second spring end 30 is fixedly connected it may pivot around a third pivot joint 32 facilitating that the spring device 15 may be angled to the intended angle.

In the present embodiment the spring device 15 is a gas spring. In other embodiments the spring device may comprise a spring coil, a hydraulic cylinder, or similar spring-loaded elements, or any combinations thereof.

The predetermined spring force is at least 150 N, and in an embodiment the spring force is 200 N. The predetermined spring force is chosen in relation to the different weights of the treatment device, hence the heavier treatment device 2 the higher predetermined spring force, however, the flexibility in different weights of the treatment device 2 is also obtained by the variable connection 31 as will be further described below.

The variable connection 31 may be stepless or it may have a plurality of predetermined positions as shown in FIGS. 3 and 4.

As mentioned above, each predetermined position of the variable connection 31 corresponds to a weight of the treatment device 2 so that the treatment device is balanced to a degree wherein it exerts a slight pressure to a head of a patient.

The angles may be between 3 degrees and 20 degrees. However, other angles may be chosen in view of the weights of the treatment device.

The variable connection 31 may comprise a connection member 33 being arranged at the first arm end 5, the connection member 33 is configured to receive the first spring end 29 as seen in FIG. 3. In the present embodiment, the connection member 33 is connected to the second part end 9 and is connected to the first arm end 5 via the first pivot joint 10. Hence, the connection member 33 is configured to connect the second part end and the first arm end. The second part end 9 is securely connected to the connection member via bolt connections. By having a securely connection between the connection member and the stepper part a support for the spring device is obtained. Since the balance arm 4 can be moved in view of the connection member 33 via the first pivot joint 10 it is ensured that the spring device 15 may be positioned correctly without any misalignment.

The connection member 33 comprises a recess 34 wherein a pin 35 of the first spring end 29 is movable arranged. In the present embodiment the recess 34 has an extension extending away from the balance arm 4 in an angle compared to the longitudinal axis 11 of the balance arm 4. The recess 34 has a plurality of indentations 36 arranged along the extension of the recess 34 as best seen in FIG. 4, the pin 35 is configured to be moved into one of the indentations 36 and thereby position the spring device 15 in the intended angle in relation to the longitudinal axis 11. In the present embodiment six indentations 36 are arranged in connection with the recess 34, however other numbers of indentations may be incorporated into the connection member 33. In the present embodiment, the spring device 15 may be positioned in the intended indentation by the operator in view of the treatment device to be used.

In another not shown embodiment, the connection member may be operatively connected with a control unit (not shown). The control unit may be configured to position the spring device in an angle by instruction of the operator, or automatically by identifying a weight of the treatment device. The angulator device may also comprise a sensor for identifying a weight of the treatment device when mounted on the angulator device. The sensor transmit data to the control unit and on basis of the data, the control unit may position the spring device for balancing the weight.

In FIG. 3, the stepper part 7 comprises a first step member 37 and a second step member 38. Each step member 37, 38 is connected to a slide mount 39 of the slide part 18 with a mutual distance between them. The first step member 37 is connected with the slide mount 39 via the second pivot joint and the second step member is connected to the slide mount 39 by a bolt connection. The second step member 38 comprises a plurality of holes 40 in the opposite end of the end being connected to the slide mount 39. The lock pin (not shown) is configured to be introduced into one of the holes 40 when the angle of the stepper part 7 is arranged in its intended position. When the lock pin is out of engagement of the holes 40 the second step member 38 may be moved up and down compared to the first step member 37 whereby the angle of the stepper part 7 is changed by it is moved around the second pivot joint.

In FIGS. 5 to 7, an embodiment of the slide part and movement member 22 is shown. FIG. 5 shows an exploded view of the movement member 22. The movement member 22 is configured to releasable maintain the slide part (not shown) in an intended position. In the present embodiment the intended position is meant angles in 360 degrees around a centre of the movement member 22, and not in a vertical direction.

The movement member 22 comprises a ball 41 having a through-going bore 42 wherethrough the slide part is extending. A bolt (not shown) may be inserted into the ball 41 and through the slide part so that the slide part is securely connected to the ball 41. The movement member 22 also comprises an upper ball seat 43 and a lower ball seat 44 partly surrounding the ball 41. Each ball seat 43, 44 are supported by a housing comprising upper housing element 45 and lower housing element 46. The upper housing element 45 and lower housing element 46 are connected to each other by screws 47.

In FIG. 6 the movement member 22 is assembled. In the upper housing element 45 a first adjustment opening 48 is arranged. The first adjustment opening 48 is arranged opposite a corresponding second adjustment opening 49 arranged in the lower housing element 46. The lower adjustment opening 49 may be arranged with an internal thread so that and operating bolt 50 (seen in FIG. 7) may be inserted through first adjustment opening 48 and into second adjustment opening 49. The bolt having a tread being configured to go into engagement with the internal thread. In connection with the bolt 50, a handle 51 is arranged. By moving the handle 50 to either side in FIG. 7, the upper housing element 45 and lower housing element may either be pushed together wherein the ball seats fixate the ball in a first position wherein the slide part is securely fastened (cannot be angled), and being released so that the ball seats allow the ball to be moved in relation to the ball seats, i.e. a second position wherein the slide part is movable (can be angled in any direction). The movement member 22 is also configured to allow intermediate positions between the completely locked first position and the released situation in second position. In these intermediate positions, a minor pressure is applied to the ball enabling movement of the slide part using a higher force than when the handle is its second position.

In the present embodiment, the handle 51 is configured to manually controlling the locking member 22.

In another not shown embodiment, the locking member may be operatively connected with a control device, the control device being configured to allowing the slide part to be moved (angled) with activation, and to lock the slide part in position when the control device is deactivated.

In addition, restrictions in movement of the slide part are obtained by a predetermined opening 52 as seen in FIG. 6 in the upper housing element 45, the slide part is extending through the opening 52 and will be restricted in further movement by a circumference 53 of the opening 52 in all directions so that when the slide part abuts the circumference 53 it is hindered in being moved further. The slide part is movable in all directions within the opening 52. The geometry of the opening 52 is in the present embodiment defined by two half-circles connected by straight lines. Hereby is obtained that the slide part can be angled more in the direction between the two half-circles than in the direction being perpendicular thereto. The opening may be defined with other shapes and geometries whereby the room for movement and angling of the slide part may be adjusted.

As mentioned above, the treatment device is a coil, and wherein the coil is configured to TMS (Transcranial Magnetic Stimulation). The coil may be operatively connected with a magnetic stimulator.

Although the invention has been described in the above in connection with preferred embodiments of the invention, it will be evident for a person skilled in the art that several modifications are conceivable without departing from the invention as defined by the following claims.

The invention claimed is:

1. A balancing, positioning and fixating assembly for balancing a treatment device, comprising
   a balance arm having a first arm end and a second arm end,
   a stepper part having a first part end and a second part end,
   the first arm end is connected with the second part end via
      a first pivot joint so that the balance arm is movable in relation to the stepper part, and
   an angulator device is arranged in connection with the second arm end, the angulator device is configured to connect the treatment device to the balance arm and to facilitate movement of the treatment device in different angles, the angulator including a joint movable independent of the position of the balance arm, the angulator including a joint movable independent of the position of the balance arm,
   wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm, wherein the variable connection includes a connection member connected to the first arm end via the first pivot joint, wherein the variable connection includes a connection member connected to the first arm end via the first pivot joint,
   further comprising the treatment device, wherein the treatment device is a coil.

2. The balancing, positioning and fixating assembly according to claim 1, wherein the spring device is a gas spring.

3. The balancing, positioning and fixating assembly according to claim 1, wherein the variable connection is stepless or has a plurality of predetermined positions.

4. The balancing, positioning and fixating assembly according to claim 1, wherein each predetermined position of the variable connection corresponds to a weight of the treatment device so that the treatment device is balanced to a degree wherein it exerts a slight pressure to a head of a patient.

5. The balancing, positioning and fixating assembly according to claim 1, wherein the connection member is arranged at the first arm end, and wherein the connection member is configured to receive the first spring end.

6. The balancing, positioning and fixating assembly according to claim 1, wherein the connection member comprises a recess in which a pin of the first spring end is movable arranged.

7. The balancing, positioning and fixating assembly according to claim 6, wherein the recess has an extension extending away from the balance arm in an angle compared to the longitudinal axis of the balance arm.

8. The balancing, positioning and fixating assembly according to claim 1, wherein the angulator device comprises a ball joint configured to allow the treatment device to be moved around the ball joint in any angle.

9. The balancing, positioning and fixating assembly according to claim 1, further comprising a chair configured to support at least the stepper part.

10. A balancing, positioning and fixating assembly for balancing a treatment device, comprising
a balance arm having a first arm end and a second arm end,
a stepper part having a first part end and a second part end,
the first arm end is connected with the second part end via a first pivot joint so that the balance arm is movable in relation to the stepper part, and
an angulator device is arranged in connection with the second arm end, the angulator device is configured to connect the treatment device to the balance arm and to facilitate movement of the treatment device in different angles,
wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm,
wherein the variable connection includes a connection member and a recess, and wherein the recess has a plurality of indentations arranged along the recess, and wherein a pin is configured to be moved into each of the indentations and thereby position the spring device in the intended angle in relation to the longitudinal axis.

11. A balancing, positioning and fixating assembly for balancing a treatment device, comprising
a balance arm having a first arm end and a second arm end,
a stepper part having a first part end and a second part end,
the first arm end is connected with the second part end via a first pivot joint so that the balance arm is movable in relation to the stepper part, and
an angulator device is arranged in connection with the second arm end, the angulator device is configured to connect the treatment device to the balance arm and to facilitate movement of the treatment device in different angles,
wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm, and
wherein the stepper part is configured to be moved between a first extreme position and a second extreme position.

12. The balancing, positioning and fixating assembly according to claim 11, wherein the stepper part comprises a locking pin being configured to lock the stepper part in either the first extreme position or the second extreme position or any positions therebetween.

13. A balancing, positioning and fixating assembly for balancing a treatment device, comprising
a balance arm having a first arm end and a second arm end,
a stepper part having a first part end and a second part end,
the first arm end is connected with the second part end via a first pivot joint so that the balance arm is movable in relation to the stepper part, and
an angulator device is arranged in connection with the second arm end, the angulator device is configured to connect the treatment device to the balance arm and to facilitate movement of the treatment device in different angles,
wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm,
further comprising a slide part having a first slide end and a second slide end, the first part end of the stepper part is connected with the second slide end via a second pivot joint.

14. The balancing, positioning and fixating assembly according to claim 13, wherein a movement member is arranged between the first slide end and the second slide end, the movement member is configured to releasably maintain the slide part in an intended position.

15. The balancing, positioning and fixating assembly according to claim 14, wherein the movement member has a first position wherein the slide part is securely fastened and a second position wherein the slide part is movable.

16. The balancing, positioning and fixating assembly according to claim 15, wherein a locking member configured to lock the movable member in the first position.

17. The balancing, positioning and fixating assembly according to claim 15, wherein the movement member comprises a ball wherethrough the slide part is extending.

18. The balancing, positioning and fixating assembly according to claim 14, wherein the movement member is configured to be securely mounted on a back of a backrest of a chair.

19. The balancing, positioning and fixating assembly according to claim 13, wherein restrictions in movement of the slide part are obtained by a predetermined opening in a housing, the slide part is extending through the opening and will be restricted in further movement by a circumference of the opening in all directions so that when the slide part abuts the circumference it is hindered in being moved further.

20. The balancing, positioning and fixating assembly according to claim 13, wherein a counterweight is connected with the first slide end.

21. A balancing, positioning and fixating assembly for balancing a treatment device, comprising
- a balance arm having a first arm end and a second arm end, wherein the balance arm consists of only a single arm,
- a stepper part having a first part end and a second part end,
- the first arm end is connected with the second part end via a first pivot joint so that the balance arm is movable in relation to the stepper part, and
- an angulator device is arranged in connection with the second arm end, the angulator device is configured to connect the treatment device to the balance arm and to facilitate movement of the treatment device in different angles,
- wherein a spring device having a predetermined spring force is arranged along the balance arm, the spring device has a first spring end and a second spring end, the second spring end is fixedly connected to the balance arm closer to the second arm end than the first arm end, and the first spring end is connected with the first arm end via a variable connection so that the spring device can be arranged in different angles compared to a longitudinal axis of the balance arm,
- further comprising the treatment device, wherein the treatment device is a coil.

* * * * *